United States Patent [19]

Weiss

[11] 4,037,965

[45] July 26, 1977

[54] METHOD AND OPTICAL MEANS FOR DETERMINING DIMENSIONAL CHARACTERISTICS OF THE PARTICLE DISTRIBUTION IN A COLLECTION OF PARTICLES

[75] Inventor: Edward Leonhardt Weiss, Quakertown, Pa.

[73] Assignee: Leeds & Northrup Company, North Wales, Pa.

[21] Appl. No.: 669,788

[22] Filed: Mar. 23, 1976

[51] Int. Cl.$^2$ ............................................. G01N 15/02
[52] U.S. Cl. .............................. 356/102; 350/162 SF; 356/103
[58] Field of Search .......................... 356/71, 102, 103; 350/162 SF

[56] References Cited

U.S. PATENT DOCUMENTS

| | | | |
|---|---|---|---|
| 3,809,478 | 5/1974 | Talbot | 356/102 X |
| 3,835,315 | 9/1974 | Gravitt, Jr. | 356/103 X |
| 3,873,206 | 3/1975 | Welcock | 356/102 X |

Primary Examiner—John K. Corbin
Assistant Examiner—Matthew W. Koren
Attorney, Agent, or Firm—William G. Miller, Jr.; Raymond F. MacKay

[57] ABSTRACT

The far-field diffraction pattern produced by illuminating a collection of particles with a coherent light source is spatially modulated by a filter mask having a first aperture. The aperture is shaped to pass a total light flux proportional to a particular moment of the particle distribution over a certain particle size range. Light flux is passed by another aperture at greater or lesser radii and adjacent the first aperture. That flux is effectively subtracted from the flux passed by the first aperture as by subtracting the resulting signals produced by a photo detector at different times in response to the flux passed by the filter. The difference signal provides a measure of the particular moment within the same limits of accuracy but over a wider or narrower particle size range, respectively.

12 Claims, 6 Drawing Figures

METHOD AND OPTICAL MEANS FOR DETERMINING DIMENSIONAL CHARACTERISTICS OF THE PARTICLE DISTRIBUTION IN A COLLECTION OF PARTICLES

BACKGROUND OF THE INVENTION

The principle of the determination of dimensional characteristics of particle distribution from measurements of forward light scattering has been recounted many times. Briefly, the particle distribution is illuminated by a coherent light beam, its far-field diffraction pattern is formed, and the light in this pattern is spatially modulated before detection in such a manner that the output signal is proportional to some desired characteristic of the distribution. As was taught by Stetter in STAUB, 30, 225, 1962 in the article entitled "Uber integrale optische Staubmessung" a spatial modulation of the far-field diffraction pattern in accordance with the reciprocal of the radius from the center of the pattern, as by using a split shaped aperture in a spatial filter, gives a total flux transmission proportional to the volume of the particles. Stetter also suggests that the difficulty of filtering out the light beam from the central area of the pattern can be compensated for to some degree by expanding the slit at its centrally located end.

In U.S. Pat. No. 3,809,478 issued to John Henry Talbot on May 7, 1974, there is set forth an equation for the transfer function of a filter for determining the $n$'th moment of a particel distribution by number. That equation indicates that the transmission factor of the filter at any point should be directly related to the $(2-n)$th power of the radial dimension of that point. That transfer function, of course, gives the same shape for a filter aperture for determining the total volume of the particles as suggested by Stetter in his 1952 publication and the Talbot description suggests that the equation adequately defines filters for determining other moments.

As set forth in U.S. Pat. No. 3,873,206 issued to William Leslie Wilcock on Mar. 25, 1975, it is necessary to not only compensate for the inability to utilize the central portion of the far-field diffraction pattern because of the presence of the incident light beam in that area, but it is also necessary to compensate for the outer limits of the filter which is used to spatially modulate the diffraction pattern. Compensation relating to the outer limits of the filter is necessary because of vignetting by the collector lens or loss of light flux which occurs because of the finite size of the filter mask as dictated by the size of the collecting lens receiving the scattered light.

The method of determining the dimensional characteristics of particle distribution from measurements of forward scattered light is most simply understood in the context of particles of spherical shape. For such a particle whose radius $a$ is sufficiently large compared wth the wavelength $\lambda$ of the incident beam, the radial intensity distribution in the far-field diffraction pattern is $$I(w,a) = Ek^2 a^4 [J_1(kaw)/kaw]^2 \qquad (1)$$

where $E$ is the flux per unit area in the incident beam, $k = 2\pi/\lambda$, $w = \sin\theta$ with $\theta$ the angle relative to the direction of the incident beam, and $J_1$ is the first-order Bessel function of the first kind. If this distribution is spatially modulated by a function $T(w)$, the integrated signal from a particle of radius $a$ is $$S(a) = C_1 \int_o^1 I(w,a) T(w) 2\pi w\, dw$$
$$= C_2 a^2 \int_o^1 w^{-1} T(w) J_1^2(kaw) dw \qquad (2)$$

where the $C$'s are instrumental constants.

Suppose now that it is desired to have the signal S proportional to the nth power of the radius of the particle, i.e., $$S \propto a^n. \qquad (3)$$

It is clear from (2) that (3) is secured if $$\int_o^1 w^{-1} T(w) J_1^2(kaw) dw = K_n a^{n-2} \qquad (4)$$

where $K_n$ is a constant involving $k$. This integral equation (4) defines the required modulation function $T(w)$, and the essential problem of the method is to find a solution of (4) which is valid for the range of $a$ which is of interest, but which also satisfies the physical constraints of a practical instrument.

To illustrate this problem consider the modulating function $$T_3(w) = b_3 w^{-1}, 0 \leq w \leq 1 \qquad (5)$$

where $b_3$ is a constant. Substitution in the left hand side of (4) gives $$\int_o^1 w^{-1} T_3(w) J_1^2(kaw) dw = b_3 \int_o^1 w^{-2} J_1^2(kaw) dw$$
$$= b_3 ka \int_o^{ka} x^{-2} J_1^2(x) dx$$

where $x$ has been used to replace $kaw$. For values of particle diameter $a$ which are large enough for the expression (1) to be valid, $\int_o^{ka} x^{-2} J_1^2(x) dx$ is negligibly different from $\int_o^\infty x^{-2} J_1^2(x) dx = 4/3\pi$. Hence $$\int_o^1 w^{-1} T_3(w) J_1^2(kaw) dw = [(4b_3 k\pi)/3] a,$$

and comparing this with (4) it apperas that the modulating function of (5) is a solution of (4) for $n = 3$, i.e., that it leads to a response proportional to the third power of the radius, and so proportional to the volume, of the particle. In a similar way it can be shown that the family of modulating functions $$T_n(w) = b_n w^{2-n}, 0 \leq w \leq 1 \qquad (6)$$

where $n = 1, 2, \ldots$ lead to responses proportional to the first, second, . . . powers of the radius of the particle.

Unfortunately these modulating functions do not represent possible solutions for a practicel instrument, because they require $T(w)$ to have non-zero values over the whole range of $w$ from zero to unity. Now the central region of the diffraction field, where $w$ is near zero, is not usable because it contains the light from the unscattered beam, which must as far as possible be excluded from the measurement. In consequence $T(w)$ must be zero for values of $w$ less than some value $w_i$ which is determined by the optical characteristics of the illuminating beam and the acceptable level of unscattered light. Similarly, the geometrical configuration of the instrument sets an upper limit $w_o$ to the angular field over which the diffracted light can be collected, which means that $T(w)$ must be zero for values of $w$ greater than $w_o$. In practice the choice of modulating functions is thus restricted to those which satisfy the condition that $T(w)$ is non-zero only for $w_i \leq w \leq w_o$, so that in place of (4) the integral equation defining T can be written $$\int_{w_i}^{w_o} w^{-1} T(w) J_1(kaw) dw = K_n a^{n-2} \qquad (7)$$

Experience shows that the family of functions represented by (6) is never an optimum solution of (7), and for some values of $n$ it does not even provide useful approximation in the sense that there is no reasonable range of particle sizes for which S is approximately proportional to $a^n$. The most favorable case is with $n = 2$, which corresponds to T = constant. The further $n$ is from 2 the further the response departs from the desired proportionality to $a^n$. The droop with increasing $a$ is due to the inner limit $w_i$, because a larger proportion of the light scattered by larger particles is in the unusuable central part of the field. Similarly the droop for smaller values of $a$ is due to the outer limit $w_o$ because a larger proportion of light from smaller particles is scattered outside the angular limits of the instrument.

It is possible to obtain greatly improved solutions of (7) by dividing the range from $w_i$ to $w_o$ into two or more parts in each of which T takes the form of a polynomial in $w$ (or $\theta$), viz.

$$T(w) = \alpha_1 + \beta_1 w + \gamma_1 w^2 + \ldots, w_i < w < w_1,$$
$$= \alpha_2 + \beta_2 w + \gamma_2 w^2 + \ldots, w_1 < w < w_2,$$
$$= \alpha_p + \beta_p w + \gamma_p w^2 + \ldots, w_{p-1} < w < w_o,$$

where $\alpha_1, \alpha_2 \ldots, \beta_1, \beta_2 \ldots, \gamma_1, \gamma_2 \ldots$ are constants. Optimum values of these coefficients can be chosen, for example, by requiring that the root-mean-square departure from the desired power of particle radius $a$ be minimized over a selected range of particle radius $a$.

The solution of this problem depends on the recognition of a new concept regarding the modulating functtion "T". Hitherto the modulation of the diffraction pattern has been thought of in terms of optical spatial filtration (or its electrical equivalent); the intensity is altered at particular points by passing the diffracted flux through a filter whose transmission is characterized by the chosen function "T". Since the transmission is essentialy zero or positive this process confines the choice of "T" to functions which are everywhere positive. If "T" can take values which are negative a greatly enlarged choice of functions becomes available for the solution of (7). This is the essence of the advance which is exemplified by this invention and which has allowed the development of an improved method and means for determining dimensional characteristics of a particle distribution for the cases of $n > 2$ over a broad range of particle sizes and for sharpening the cut-off of the response characteristic at the large particle end of the characteristic for broad and limited particle size ranges.

Thus, it has been found that the teaching of others provides an adequate method and means for obtaining some of the lower moments, such as the second and third moments, of a particle distribution by number, which would be respectively proportional to the summations of the second and third powers of the diameter of the particles in the collection if the range of particle sizes is limited. However, even the third moment cannot be satisfactorily obtained for a very broad range of particle sizes with a single aperture filter as taught by others, because the effect of the inner limit of the mask is increasingly severe for the higher moments. It is therefore an object of this invention to provide a method and means for improving the analysis of a collection of particles to determine particular dimensional characteristics of the particles in the collection. More particularly, it is an object of this invention to provide a method and means for improving the determination of the third and fourth moments by providing means for compensating for the physical limits of the filter and extending the response in the large particle region as well as sharpening the cut-off of the response characteristic in that region.

SUMMARY OF THE INVENTION

In carrying out this invention there is provided means to perform the method for improving the analysis of the collection of particles to determine a particular dimensional characteristic of the distribution of particles in the collection. That method includes the step of passing a light beam though the collection as well as the step of measuring a portion of the low-angle, forward-scattered light flux which results from the diffraction of the light beam by the particles in the collection and modulating the response of that measurement as a function of the angle of diffraction of the flux being measured so that the response to the flux diffracted by each particle is such that the total flux measured is proportional to the desired moment or dimensional characteristic. The modulating function necessarily has a range of values such that, through the span of the diffraction angles over which the response is modulated, the function has a range of values which includes both negative and positive values and may specifically, for example, have a positive value for a range of the smallest diffraction angles and a negative value for a range of angles adjacent the smallest range of angles.

DESCRIPTION OF THE PREFERRED EMBODIMENTS

Figure 1:
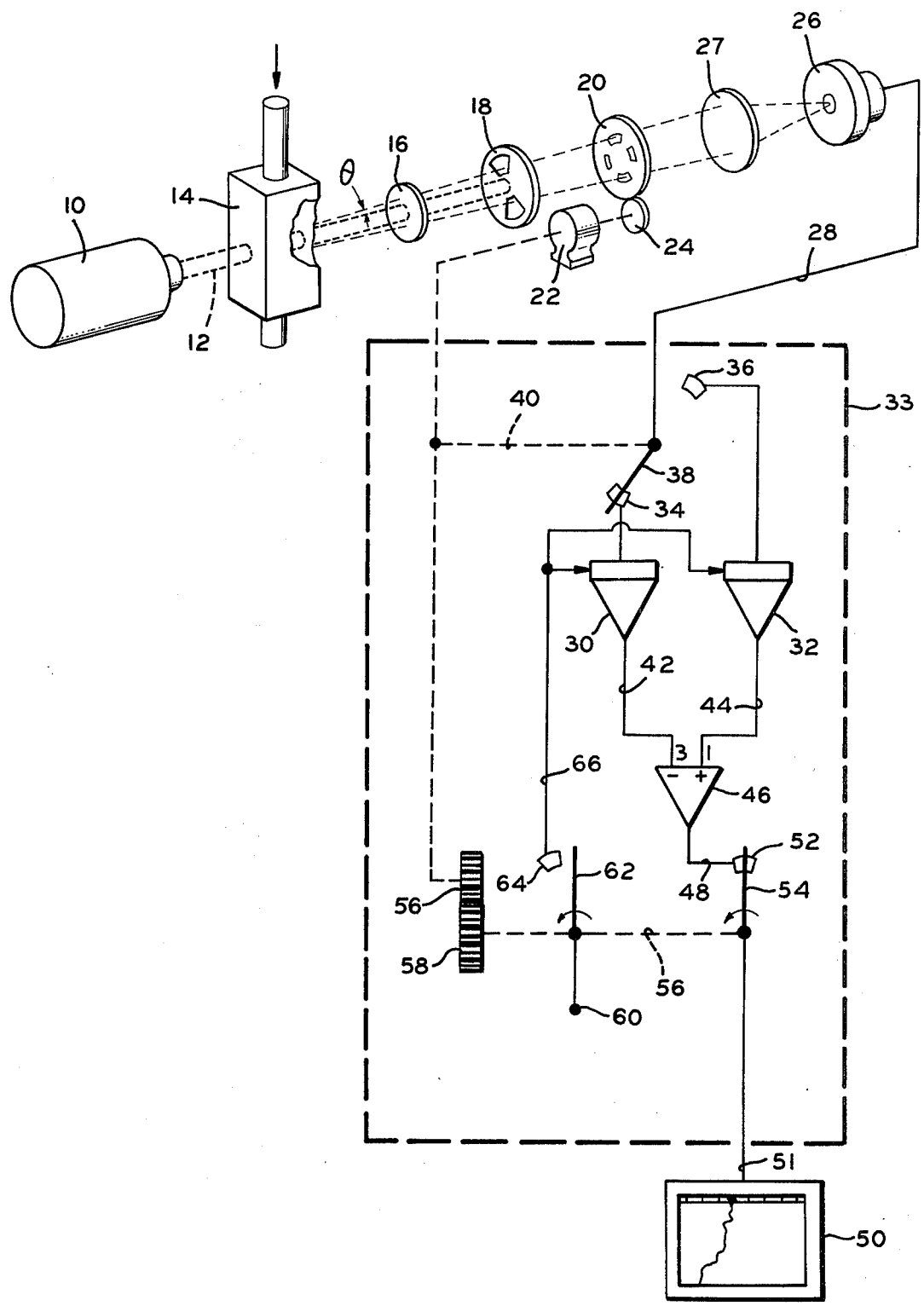
FIG. 1 is a drawing in perspective showing an optical system which can be utilized in carrying out this invention as well as a block diagram of a computer circuit which can be used for making the measurement of a particular moment of the particle distribution in the particle collection being examined.

In FIG. 1 a coherent light source shown as laser 10 provides a monochromatic light beam 12. The light beam is directed through a sample container 14 which contains the collection of particles whose dimensional characteristics are to be measured. The measurement may, for example, be in terms of a particular moment of the particle distribution by number. The sample chamber may be in a flow path whereby fluid suspended particles are constantly flowing through the chamber or the sample may comprise a fixed collection. In some circumstances the particle collection may consist of a planar sample of particles or a photographic image of them.

The light from the laser is diffracted by the particles in the collection and the low-angle, forward-scattered light flux diffracted over the solid angle $\theta$ is collected by the collecting lens 16 and a fraction of the light passed by the lens 16 is transmitted though the chopping blade 18 which is shown as having two sectors substantially pie-shaped and oriented 180° from each other. These sectors are each of sufficient angular span to allow the diffracted light to pass through a set of apertures in the filter mask 20 which apertures are oriented 180° from each other.

The mask 20 is located in the Fraunhofer plane of the lens 16 and is rotated as shown in FIG. 1 by a motor 22 through a friction drive element 24.

When the diffracted light passes through the transparent or open sectors of the chopping blade and passes through the spatial filter apertures it is directed onto the photo detector 26 by the field lens 27. The detector then produces a signal output on line 28 which is directly related to the total amount of light flux passed by the spatial filter 20. The signal on line 28 is introduced as an input to a computer 33 which calculates the moment in accordance with the design of the mask 20 being used. The calculation involved is basically the subtraction of the signal on line 28 resulting from the transmission characteristic of one or more apertures exposed at a particular time from the signal resulting from the transmission characteristic of at least one other aperture exposed at a different time. The computer 33 can therefore have any of a number of forms. It may, for example, be a microcomputer or it may be an analog type computer as shown in FIG. 1 for simplicity of description.

In the circuit of FIG. 1 the signal on line 28, is sequentially connected for short periods of time to the input of integrating amplifiers 30 and 32 of computer 33 through the respective contacts 34 and 36 by way of the contact 38 which is rotated by shaft 40 of motor 22 in synchronism with the rotation of the filter mask 20. The making of the rotating contact 38 and contact 34 is synchronized to correspond with the passage of light through the sections of the chopping blade 18 and a particular set of apertures in the mask 20. Similarly, when the moving contact 38 is in contact with the contact 36 the light passing through the apertures of the chopping blade 18 passes through another set of apertures in the mask 20. The amplifiers 30 and 32, therefore, are effective to average over a number of rotations of contact 38 the amount of light passing through the respect apertures in the mask 20 so that there is provided on lines 42 and 44, respectively, signals proportional to the average light passing through the sequentially exposed apertures in the mask 20. Those signals are compared by the differential amplifier 46 to provide an output on line 48 representative of the difference between the light transmitted by the separate apertures or sets of apertures in the mask 20. That signal is then passed to a recorder 50 by way of line 51 and the contact made between the fixed contact 52 and the rotating contact 54. Thus, it may be said that the detector 26 in conjunction with computer 33 and recorder 50 measures a portion of the forward scattered light flux and the apertures of the filter mask 20 in conjunction with the computer 33 modify or modulate that measurement as a function of the angle of diffraction $\theta$. The modification and modulation results from the spatial filtering effected by mask 20 and further modification and modulation occurs as a result of calculations in computer 33.

The rotating contact 54 is rotated by the shaft 56 in synchronism with the rotation of the contact 38 by shaft 40. However, the period of the rotation is greater because of the gear reduction accomplished by the gears 56 and 58. Thus, the rotation of the contact 38 is effective to produce signals on lines 42 and 44 which represent an average over a number of samples of the light transmitted by the two sets of apertures in filter mask 20. Amplifier 46 produces a signal related to the difference in the average light transmitted by the apertures exposed at different times and provides that signal on line 48.

The rotation of the contact 54 is synchronized in accordance with the number of samples to be considered in each average so that the average can then be indicated and recorded by the instrument 50. Upon a measurement of the signal on line 48 by the instrument 50 there is a need for resetting the amplifiers 30 and 32. This is acomplished by the introduction of a rest signal into those amplifiers. The source of the rest signal is connected to the terminal 60 and thence through the rotating contact 62 and fixed contact 64 to the reset line 66 which is connected to both amplifiers 30 and 32.

As will be evident from FIG. 1, the rotating contact 62 is rotated by shaft 56 in sychronism with a rotation of contact 54 so that after each average value signal on line 48 is measured by the instrument 50 the amplifiers 30 and 32 are reset so that the subsequent rotation of the contact 38 throughout the period it takes for one rotation of the contact 54 is effective to produce a new average on line 48 of the difference between the light flux passed by filter apertures exposed at one time and that passed by the apertures exposed at another time as with filter 20.

The filter 20 of FIG. 1 may take any one of a number of forms depending upon the particular dimensional characteristic or the particular moment of the particle distribution which it is desired to measure with the instrument 50 of FIG. 1. For example, in FIG. 2 there is shown a front elevation of the type of mask which may be utilized as the filter 20 to obtain a measurement of the third moment. The aperture shown in solid line form as aperture 70 in the solid circular mask will provide a signal from the detector 26 of FIG. 1 on line 28 which is proportional to the third moment of the particle distribution being examined in accordance with the teaching of U.S. Pat. No. 3,873,206 which is hereby incorporated by reference.

It will be evident that the aperture 70 includes an area shown as a portion of an annulus adjacent the central portion of the mask for providing an enhancement of the signal in compensation for the necessity for blocking out the central portion of the diffraction pattern because of the presence of the incident beam from laser 10. The solid line aperture 70 also shows an area which is a portion of an annulus provided for enhancement at the outer extreme of the aperture for the purpose of compensating for the vignetting effect of the finite dimensions of the mask 20 and collecting lens 16.

Figure 2:
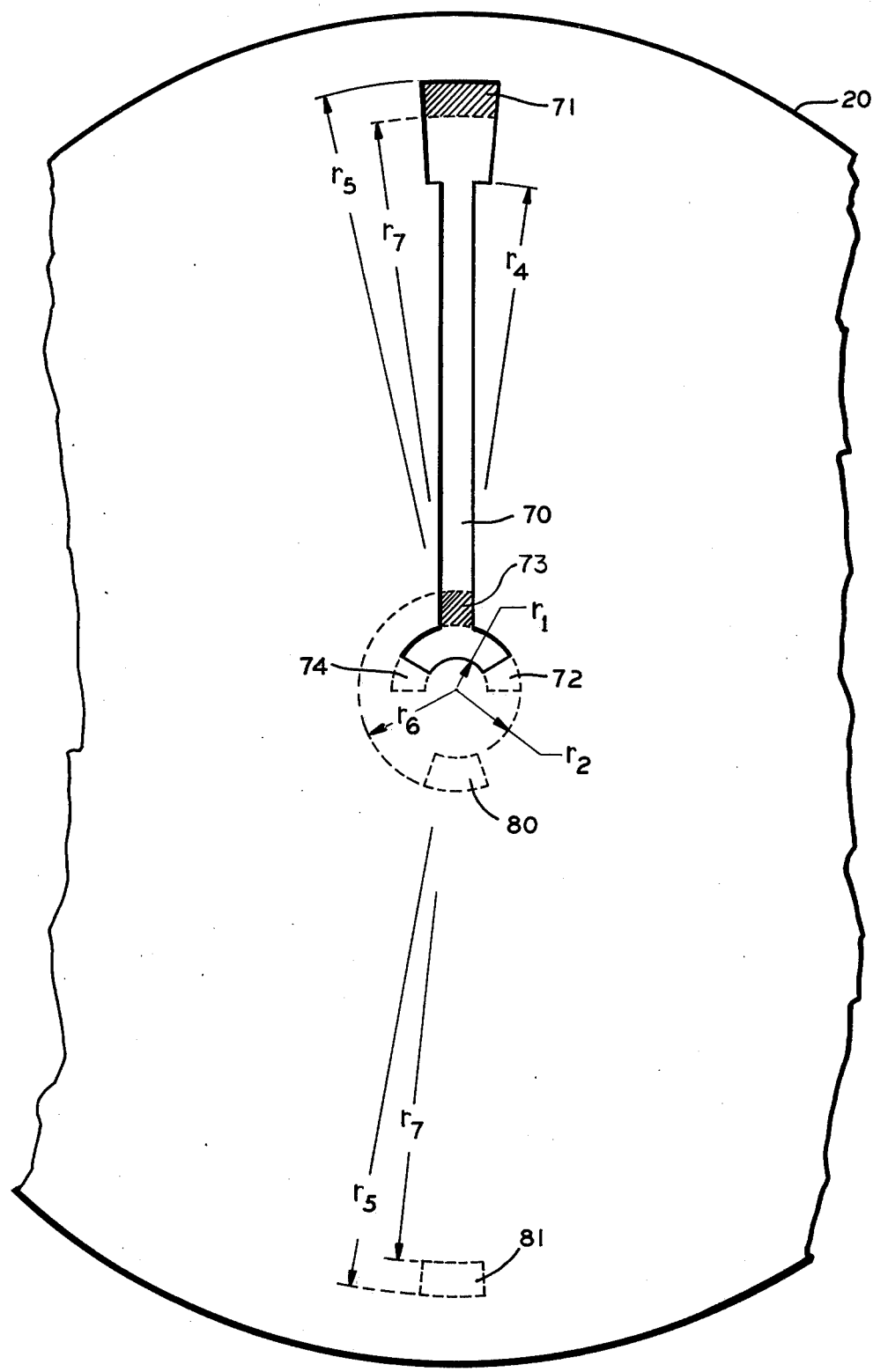
FIG. 2 is a front elevation of one form which the spatial filter may take when it is desired to provide a measurement proportional to the third moment with improved compensation for the physical limits of the filter mask.

The enhancement provided by the area adjacent the center of the mask as well as adjacent to the outer periphery of the mask, for example, may be improved upon by changing the method of measuring the third moment from that described in the Wilcock U.S. Pat. No. 3,873,206. In the present invention the transmission function can take values which are negative for particular angles of diffraction so as to allow for measurements of some of the higher amounts in a manner which will provide a measurement over a different particle size range which may be greater or smaller and more sharply defined than would be possible by methods which utilize only positive transmission functions while still maintaining the same accuracy limit of error. Thus, while the solid line aperture 70 of FIG. 2 provides a measure of the third moment of the particle distribution on line 28 of the system of FIG. 1, an improved measure of the third moment may be provided which is within the same limits of error as the measure provided by the aperture 70 but which extends over a different range of particle sizes than would be provided by the aperture 70. The different range would extend farther into the large particle region and would restrict the response in the small particle region while providing a sharper cut-off in the response in both regions. To accomplish this improved measurement there is provided an extension of the enhancement area near the center of the mask by the addition of areas shown in dashed line as areas 72 and 74 and there is provided areas 80 and 81 positioned so that flux through those areas can be measured separately.

With the arrangement of FIG. 1 and a modified chopping blade 18 the light flux passing through the aperture 70 plus the additional areas 72 and 74 is measured, for example, when contact 38 is made with contact 36. The light flux meaasured when the contact 38 is in contact with contact 34 is that which passes through the added areas 80 and 81. The chopping blade 18 would therefore have a single 180° aperture.

It will be noted that the area 80 is in a region adjacent to the areas 72 and 74 as far as its radial positioning is concerned. Thus, the outer radius of 72 and 74 is $r_2$ while the inner radius of 80 is $r_2$. The value of $(r_6-r_2)$ may advantageously be equal to the value $(r_2-r_1)$ where $r_1$ is the smallest radius usable without passing any of the incident laser beam. Thus, the area 72 and 74 pass diffracted light over the smallest range of angles while the area 80 passes diffracted light over an adjacent range of angles.

It will also be noted that area 81 has its inner and outer radii $r_7$ ad $r_5$ corresponding to the inner and outer radii of the shaded portion 71 at the outer periphery of aperture 70, which shaded portion is opaque in the improvement being described. The area of 81 may advantageously be greater than that of the shaded portion between $r_7$ and $r_5$.

The effects of the rotation of the mask 20, when constructed to have a single 180° aperture is to subtract the signal from detector 26 produced by the light flux transmitted through the aperture 80 and 81 from the signal produced by the detector 26 on line 28 due to the light flux passing through that part of the aperture 70 which omits the opaque regions 71 and 73 but includes the areas 73 and 74. It will be evident that by virtue of this subtraction the transmission function in the regions having a radii between $r_2$ and $r_6$ and between $r_5$ and $r_7$, spanned by sectors 80 and 81, is effectively negative in sign.

Figure 3:
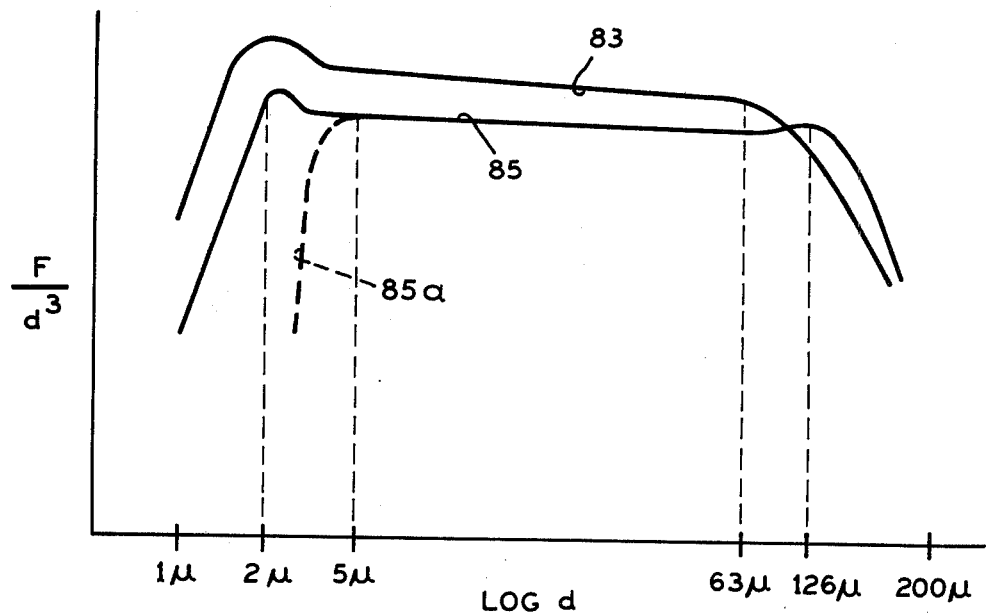
FIG. 3 is a graphical representation showing the benefits of using the mask of FIG. 2.

To illustrate the benefits to be derived from the embodiment of this invention as shown in FIG. 2 reference should be made to FIG. 3 in which there is graphically shown by curve 83 the response detector 26 to the flux transmitted by a mask aperture 70 whereas the curve 85 shows the response which would be obtained at detector 26 to the flux through the combination of apertures 70, 72 and 74 with the flux through aperture 70 subtracted and with the region 73 opaque. The curve 85 would be altered in the small particle region as shown by the curve section 85a by the effect of the flux through aperture 81 when the region 71 is opaque. Thus, a sharper cut-off is obtained along with a restricted response in the small particle region while an extended response with a sharp cut-off is obtained in the large particle region. The curves of FIG. 3 show the plot of light flux received by 26 with respect to the cube of the particle diameter versus the log of the particle diameter.

As can be seen from FIG. 3 in a typical case where the particle range from 1 micron to 200 microns is plotted the curve 83 drops off in the large particle region starting at about 63 microns whereas using the present invention the drop-off does not begin until particle size reaches 126 microns. Also, it will be noted that the cut-off of curve 85 in the large particle region is sharper than on curve 83. In contrast the drop-off in the small particle region begins at 5 microns with a sharper cut-off instead of at 2 microns as would be the case absent the benefits of the present invention.

Figure 4:
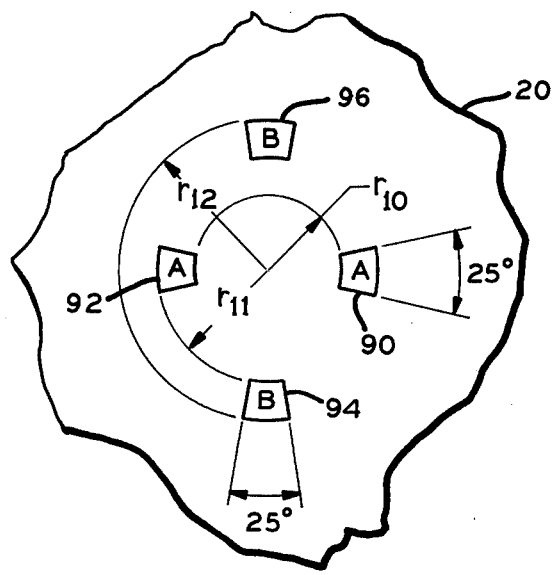
FIG. 4 is a front elevation of the central portion of a spatial filter which can be used in accordance with this invention to provide a measurement proportional to the fourth moment.

In FIG. 4 there is shown the central portion of a filter mask 20 which can be used in the system of FIG. 1. Only the center portion is shown in order to more clearly illustrate the placement of the apertures there being no other apertures in the mask other than those shown. The particular mask shown in FIG. 4 is designed for measuring the fourth moment of the particle distribution by number and it consists of a first set of apertures 90 and 92 shown as apertures A which may be pie-shaped as shown or may be substantially rectangular and have their inner radius $r_{10}$ as close to the center of the diffraction pattern as possible while still avoiding intercepting the incident beam from the laser 10. Thus, the filter mask of FIG. 4 assumes that the incident beam has a diameter less than 0.01 inches which then defines the inner radius $r_{10}$ of the sectors 90 and 92. The outer radius $r_{11}$ as shown may be, for example, 0.02 inches and the radial span of the inner portion of the apertures may be 25°, for example.

The apertures 90 and 92 will give a measurement which is a close approximation over a certain particle size range of the fourth moment. Those apertures could have their areas combined to form a single aperture, however, the use of oppositely positioned pairs of aperture serves to reduce any efforts from failure to accurately position the rotating mask 20 to turn about its center and about the center of the laser beam. The total area of the apertures 90 and 92 will normally be determined by the required signal level from detector 26. The angular extent of the aperture must, of course, not exceed the angular extent of the apertures in the chopping blade 16. Where only a single measurement is made, as taught in the Wilcock U.S. Pat. No. 3,872,206, a measurement of the light flux as close to the center of the diffraction pattern as possible provides the closest approximation to the fourth moment since the light flux in the far-field diffraction pattern at the very center of the pattern is proportional to the fourth power of the diameter of the particles. As previously pointed out, a measurement at that central portion cannot be made because of the incident light of the laser beam.

If it is desired, as with the present inventions, to make a measurement of the fourth moment within the same limits of accuracy but over a broader range of particle sizes it is necessary to add to the mask 20 the apertures 94 and 96 which, in the design shown in FIG. 4 are shown as apertures B, have their inner radius $r_{11}$ as 0.02 inches and their outer radius $r_{12}$ as 0.03 inches. The apertures 94 and 96 may desirably span an angle of 25°.

The mask of FIG. 4 incorporated in the system of FIG. 1 is arranged so that when contact 38 is in contact with contact 36 the diffracted light being passed by the sectors of the chopping blade 18 are passed through the apertures 90 and 92 of the mask 20 and as the mask is rotated the contact 38 will be caused to come in contact with contact 34 at which time the diffracted light passed by the open sectors of the chopping mask 18 is passed through the apertures 94 and 96 so that the light flux passing through the apertures 94 and 96 is effectively subtracted from that passed through the apertures 90 and 92 by subtracting the signal on line 42 of FIG. 1 from that on line 44, as previously described, by the use of the differential amplifier 46. The signals received by the amplifier may be scaled as necessary to obtain the desired extended range.

Figure 5:
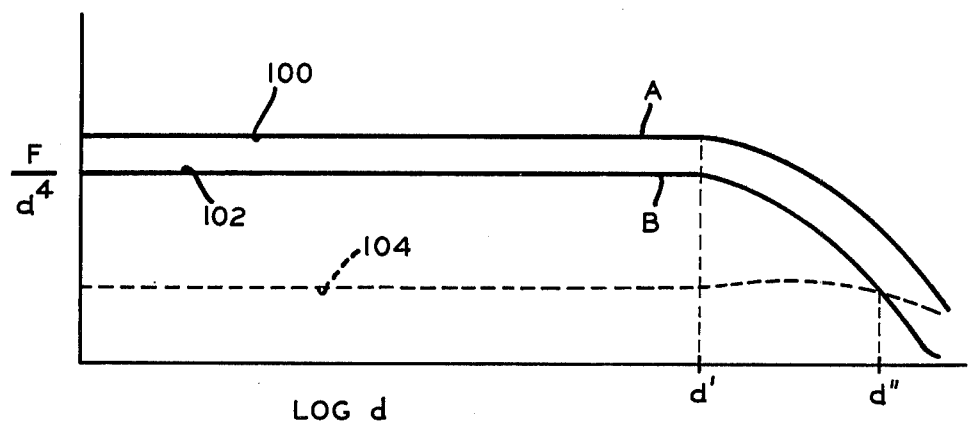
FIG. 5 is a graphical representation showing the benefits to be derived by the utilization of this invention with a mask of the type shown in FIG. 3.

To illustrate the benefits to be derived by this invention reference should be made to FIG. 5 wherein there is graphically shown the characteristic response to the apertures 90 and 92 as well as the characteristic response to the apertures 94 and 96 of the mask 20 of FIG. 4. The plot of these characteristics in FIG. 5 is shown on coordinates in which the ordinate is scaled in terms of the magnitude of the light flux detected by detector 26 divided by the fourth power of the particle diameter. Along the absicca is plotted the log of the particle diameter $d$. The characteristic 100 represents the plot which is obtained by measuring the light flux passing through the A apertures 90 and 92 for various size particles. It will be evident that the characteristic 100 is flat throughout the region plotted up to a particle size whose log is $d'$ and above that particle size the ratio of the flux to the fourth power of the diameter falls off.

The characteristic 102 plotted in FIG. 5 shows the intensity of the flux with respect to the fourth power of the diameter as it relates to the particle size where that flux is measured by the detector 26 from the light passing through the B apertures 94 and 96. The flux intensity with respect to the fourth power of the particle diameter in this characteristic also falls off after the particle size reaches a value whose log is $d'$. When the characteristic 100 has subtracted from it the characteristic 102 a characteristic 104 is obtained and it will be noted that this characteristic does not fall off until the particle size reach a greater value, namely where log $d$ is $d''$. Thus, by measuring the flux passing through apertures 90 and 92 and then subtracting from that measurement the flux passing through apertures 94 and 96, it is possible to obtain over a wider particle size range $d''$ a measure for the fourth moment of the particle distribution within the same limits of accuracy as compared with the particle size range $d'$ which is possible when making a single measurement of the light flux passing through the apertures 90 and 92. In measuring particles whose size ranges from 1 micron to 200 microns the value of $d'$ might typically be 30 microns kwhile the value of $d''$ could be 126 microns.

In making the measurement of the flux through apertures 94 and 96 a factor of 0.3 may be used to obtain the desired response as shown by curve 104 where the flux through apertures 90 and 92 is multiplied by a factor of 1.0.

Figure 6:
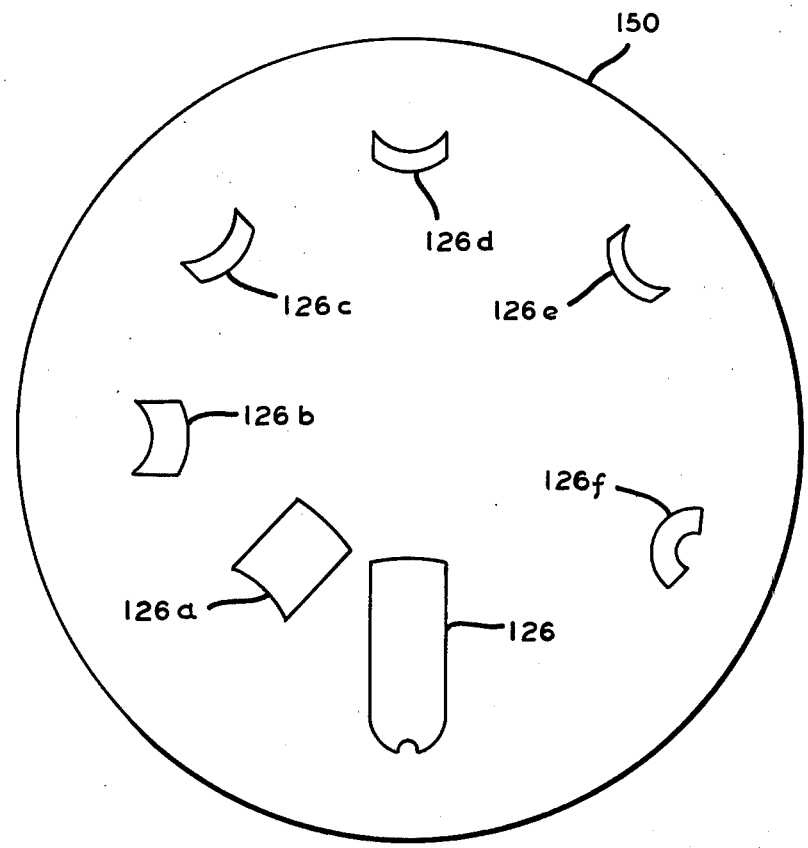
FIG. 6 is a front elevation of a multiple aperture mask for making measurements over a number of particle size ranges.

FIG. 6, which is a reproduction of FIG. 6 of the referenced U.S. Pat. No. 3,873,206 with the reference characters increased by 100, shows a filter mask which could be used in an optical system of the type shown in the present FIG. 1 if the chopping blade 18 had only one aperture and more sophisticated electronic circuitry were used for processing measurements of the flux passed by each of the apertures of mask 150, namely 126 and 126a–126f. The flux measurements through each of the apertures 126a–126f could then be compared as desired. Reference in this connection should be had to the reference U.S. Pat. No. 3,873,206 and particularly to that part between col. 5, line 20 and col. 6, line 27.

If, for example, the flux through 126f were measured and a measurement of the flux passed by 126e were subtracted, the resulting value would be a measurement with a characteristic whose range is extended in the large particle direction and has a sharper cut-off than the characteristic resulting from a measurement through 126f alone. Similarly the flux passed by other combinations of apertures can be compared with similar results.

What is claimed is:

1. The method for measuring a dimensional characteristic of the particles of a collection in a certain size range comprising the steps of:

passing a beam of light through the collection of particles, detecting the low angle diffracted light flux from said particles over a first range of diffraction angles such that the flux detected represents said dimensional characteristic over said certain size range, detecting the low angle diffracted light flux from said particles over a second range of diffraction angles such that the flux detected represents said dimensional characteristic over a lesser portion of said certain size range, and subtracting the flux detected over said second range from the flux detected over said first range to obtain as a result of said subtraction a measure of said dimensional characteristic within the same limit of error over a different portion of said certain size range than would be obtained by only detecting the flux over said first range.

2. The method of claim 1 in which said different portion is a wider portion.

3. The method of claim 1 in which said different portion is a narrower portion.

4. Apparatus for measuring a dimensional characteristic of the particles of a collection in a certain size range comprising:

means for passing a beam of light through the collection of particles, means for detecting the low angle diffracted light flux from said particles over a first range of diffraction angles such that the flux detected represents said dimensional characteristic over said certain size range, means for detecting the low angle diffracted light flux from said particles over a second range of diffraction angle such that the flux detected represents said dimensional characteristic over a lesser portion of said certain size range, and means for subtracting the flux detected over said second range from the flux detected over said first range to obtain as a result of said subtraction a measure of said dimensional characteristic within the same limit of error over a different portion of said certain size range than would be obtained by only detecting the flux over said first range.

5. Apparatus as set forth in claim 4 in which the diffracted light flux from the particles over said first range of diffraction angles includes all particles in said certain size range, and the diffracted light flux from the particles over said second range of diffraction angles includes particle of a limited size range within said certain size range so that the result of said comparison is a measure of the dimensional characteristics in said certain size range.

6. The method for improving the measurement of the moments of the particle distribution by number for a collection of particles comprising the steps of, passing a light beam through said collection, measuring a portion of the low-angle, forward-scattered light flux from the particles, modulating the response of said measurement as a function of the angle of diffraction of the flux being measured so that the response of the measurement to the flux diffracted by each particle in said light beam is such that the response of the measurement to the low-angle, forward-scattered light flux measured is proportional to the desired moment, said modulating function having a range of values such that through the span of diffraction angles over which said response is modulated the function has a positive value over one range of angles and a negative value over another range of angles.

7. Apparatus for improving the measurement in a collection of particles of the moments of the particle distribution by number comprising, means for passing a light beam through said collection, means operable to measure the total of the low-angle, forward-scattered light flux from the particles, means for modulating the response of said measurement as a function of the angle of diffraction of the flux being measured so that the response to the flux diffracted by each particle in said light beam is such that the total flux measured is proportional to the desired moment, said modulating function having a range of values such that through the span of diffraction angles over which said response is modulated the function has a positive value for a part of the span including the smallest angle and a negative value for a part of the span adjacent the part of the span including the smallest angle.

8. A method for calculating in a collection of particles the moments of the particle distribution by number comprising the steps of passing a light beam through said collection spatially modulating the low-angle, forward-scattered light flux from the beam, said spatial modulation being effected by a first filter area including the area just outside said beam with the transmission of said first filter area varying with the radius from the beam center as required to produce a total flux transmission through said filter area proportional to said moment within certain error limits and over a certain particle size range, and a second filter area adjacent said first area to produce a total transmitted flux through said second area which when subtracted from that transmitted by said first area will produce a result in effective total flux which is proportional to said moment within the said error limits over a greater range of particle sizes, and subtracting the value of total flux transmitted through said second filter area from the total flux transmitted through said first area.

9. Apparatus for improving the measurement in a collection of particles of the moments of the particle distribution by number comprising;

means for passing a light beam through said collection, means operable to measure the total of the low-angle, forward-scattered light flux from the particles, first means for modifying said measurement as a function of the angle of diffraction of the flux being measured so that response to the flux diffracted by each particle of said collection is such that the total of the flux measured approximates the desired moment within predetermined limits over a certain particle size range, and second means for modifying said measurement in sense opposite that of said first modifying means as a function of the angle of diffraction of the flux being measured so that the resulting modified measurement is proportional to said moment within said limits over a greater particle size range.

10. Apparatus as set forth in claim 9 in which said first means modifies said measurement so as to make the total flux measured substantially proportional to the third moment with the addition of flux transmission at the inner edge of the mask to provide excessive compensation for flux lost due to the inner limits of the mask, and said second means modifies the measurement as a function of the angle of diffraction of the flux over areas adjacent in radial position to the compensating area of the first means to thereby compensate for the flux lost at the inner mask limit.

11. The method for improving the measurement in a collection of particles of the fourth moment of the particle distribution by numbers comprising the steps of passing a light beam through said collection measuring the light flux falling on an annulus in the far-field diffraction pattern just outside the periphery of the light beam measuring the light flux falling on an annulus adjacent said first mentioned annulus, and subtracting said measurement of the flux falling on the last mentioned annulus from the measurement of the flux falling on the first mentioned annulus.

12. A method for measuring a value proportional to the average of the fourth power of the diameter of the individual particles making up a collection through which a beam of light has been transmitted comprising the steps of measuring a portion of the total diffracted flux intercepting the smallest usable annular area in the Fraunhofer plane outside the incident light beam measuring a portion of the total diffracted flux intercepting an annular area adjacent said smallest area, and subtracting a multiple of said last measurement from a multiple of said first measurement to produce said average of the fourth power of the diameter of the individual particles making up said collection.

* * * * *